(12) United States Patent
Ahmadzadeh Saffari et al.

(10) Patent No.: US 11,925,320 B1
(45) Date of Patent: Mar. 12, 2024

(54) ORAL CAMERA

(71) Applicants: Nadia Ahmadzadeh Saffari, Richmond Hill (CA); Arian Nabavi, Tehran (IR); Makan Nabavian, Tehran (IR); Amir Mahbod Ahmadi, Tehran (IR); Farzad Abedi Dorcheh, Isfahan (IR); Nasser Ashgriz, Thornhill (CA)

(72) Inventors: Nadia Ahmadzadeh Saffari, Richmond Hill (CA); Arian Nabavi, Tehran (IR); Makan Nabavian, Tehran (IR); Amir Mahbod Ahmadi, Tehran (IR); Farzad Abedi Dorcheh, Isfahan (IR); Nasser Ashgriz, Thornhill (CA)

(*) Notice: Subject to any disclaimer, the term of this patent is extended or adjusted under 35 U.S.C. 154(b) by 0 days.

(21) Appl. No.: 18/227,367

(22) Filed: Jul. 28, 2023

(51) Int. Cl.
- *A61B 1/00* (2006.01)
- *A61B 1/06* (2006.01)
- *A61B 1/24* (2006.01)
- *A61C 19/04* (2006.01)

(52) U.S. Cl.
CPC ........ *A61B 1/00147* (2013.01); *A61B 1/0607* (2013.01); *A61B 1/24* (2013.01); *A61C 19/04* (2013.01)

(58) Field of Classification Search
None
See application file for complete search history.

(56) References Cited

U.S. PATENT DOCUMENTS

| | | | |
|---|---|---|---|
| 2013/0286174 A1* | 10/2013 | Urakabe | A61B 1/04 348/66 |
| 2020/0053344 A1* | 2/2020 | Stegall | A61B 1/24 |

* cited by examiner

*Primary Examiner* — Rebecca A Volentine
(74) *Attorney, Agent, or Firm* — Nasser Ashgriz; UIPatent Inc.

(57) ABSTRACT

An oral camera that can view a panoramic view of all teeth in a jaw, including the front and back surfaces of teeth, as well as their top surfaces. The oral camera comprises a mouthpiece that is placed in the mouth. The mouthpiece has an inner and outer part that have mirrored surfaces. The inner and outer parts are tilted to reflect the images of the inner and outer surfaces of teeth toward an outside viewer or a camera. Thereby, a camera image comprises of images of the inner and outer surfaces of teeth as well as their top surface. Thereby allowing for inspection of all teeth for any decay or cavity.

17 Claims, 19 Drawing Sheets

ORAL CAMERA

FIELD OF THE INVENTION

The present invention relates, in general, to dental imaging devices and intra-oral cameras, and in particular, to an intraoral camera that image all teeth in a jaw at once.

BACKGROUND OF THE INVENTION

Dental cavities and gingivitis are common chronic oral diseases caused by dental plaque. Globally, between 60-90% of schoolchildren and nearly 100% adults have tooth decay, often leading to pain and discomfort. Oral conditions are the fourth most expensive to treat. Despite being remarkably widespread, oral diseases are preventable and curable if treated in time. Regular screening would help in early detection and possible prevention. However, regular screening may not be possible due to limited resources. In addition, as the world has adapted to a new normal due to the recent pandemic, frequent visits to dentist could potentially be health-threatening. Based on those considerations, checking dental health at home is financially and logically advantageous.

Intra-oral cameras are commonly used to detect dental caries and for initial diagnosis. In addition, they can be used to obtain images of teeth at different times and compare them to determine changes, such as movement of teeth.

Such cameras take closeup images of one or more teeth. These images are then stitched together to create one panoramic view of the whole jaw. There are numerous methods to stitch images together, however, they require complicated image processing algorithms that can be expensive and time consuming. Problems, such as lighting and motion, make the stitching process difficult.

An inter-oral camera that can provide the whole image of teeth eliminates the stitching issues and can provide an immediate panoramic view of the teeth.

The present device is designed to provide a panoramic view of the teeth and find and detect any change such as decay or cavity on the surfaces of the teeth.

SUMMARY OF THE INVENTION

A handheld device is disclosed that can take a panoramic view of teeth in each jaw. The device comprises of a mouth piece to be placed around the teeth. The mouth piece has a pair of mirrors, one to view the front faces of teeth, and the other to view the back faces of the teeth.

The mouth piece has a handle to allow for its placement inside the mouth. A camera is placed on a moveable stand that is attached to the handle. The moveable stand can be adjusted to aim the camera towards the mouth piece for a full view of the teeth. A light source is also provided as part of the device to provide proper lighting for the imaging. A single image taken by the camera includes both the front and back faces of the teeth through the mirrors, as well as the top surfaces of the teeth, which is directly imaged. A single image of all teeth in a jaw eliminates any need for stitching of individual images as is needed in regular inter-oral cameras. This single image allows identification of tooth positions with respect to each other and any movement of teeth during a period.

In one embodiment of the present invention, the light source comprise of fluorescence LEDs or RGB and fluorescence, utilizing UV, which excites the teeth enamel by near-UV to visible wavelength of light source. In another embodiment of the invention, light source is UV LEDs or RGB and UV both.

The present oral camera can be used by dentists to have an overall view of teeth before and during dentistry.

Another objective of the present device is to all individuals to take images of their own teeth and send it to dentist for inspection.

Another object of the present invention to use of fluorescence-based imaging, instead of white light imaging which can better identify the existence of cavities and tooth decay.

The device further comprises of an application software to analyze images and find and detect any decay or cavity on teeth. The algorithm further has a reporting system to inform a user of the health status of the teeth.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF THE DRAWINGS

FIGS. 1A, 1B, 2A, 2B, 3, 4, 5A, 5B, 6 and 7 show one embodiment of the present oral camera. The oral camera 10 comprises of three main components: the handle 20, the mouthpiece 30 and the camera stand 40. The handle 20 is ergonomically designed to be held by a user and to manipulate the mouthpiece.

Figure 5A:
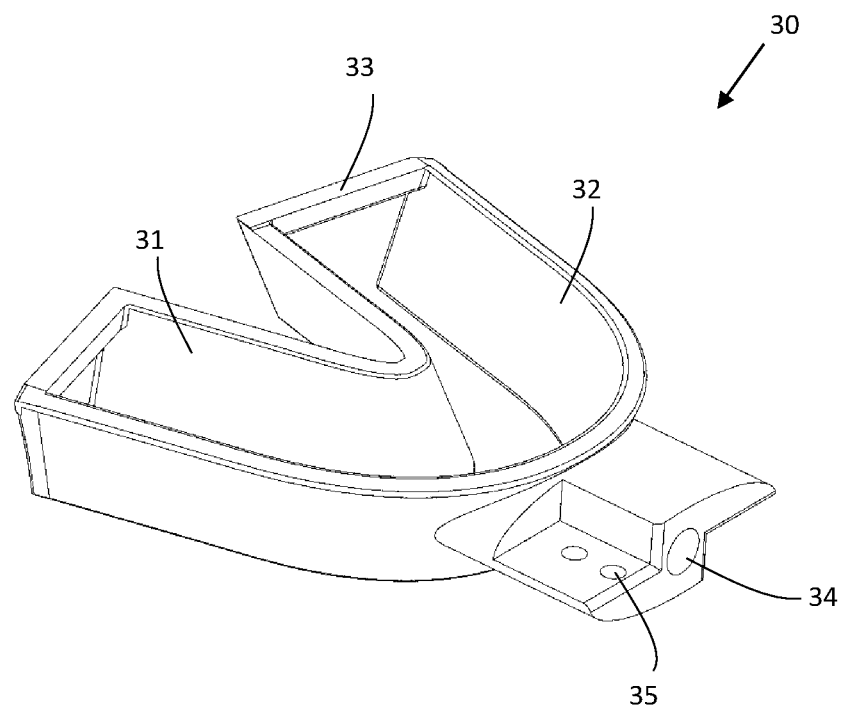
FIG. 5A shows details of the mouthpiece of the invention.
Figure 5B:
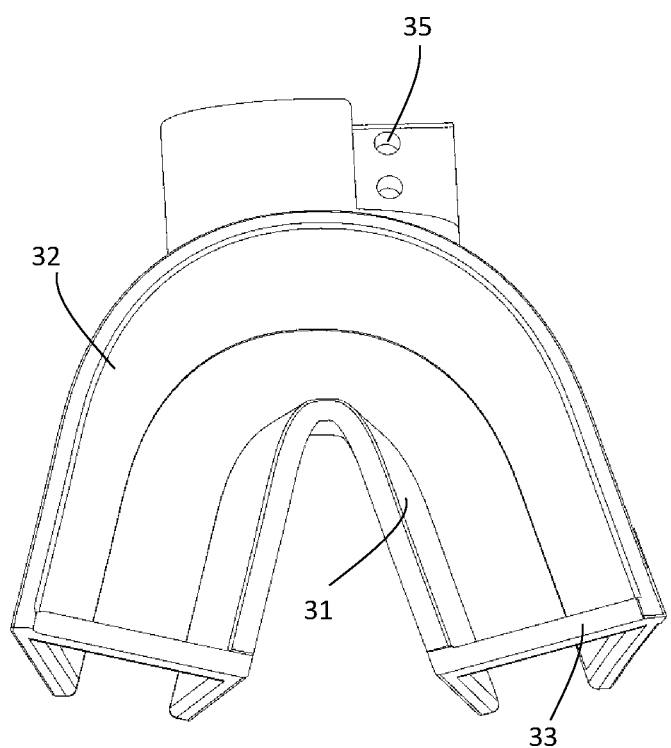
FIG. 5B shows another view of the details of the mouthpiece of the invention.
Figure 12:
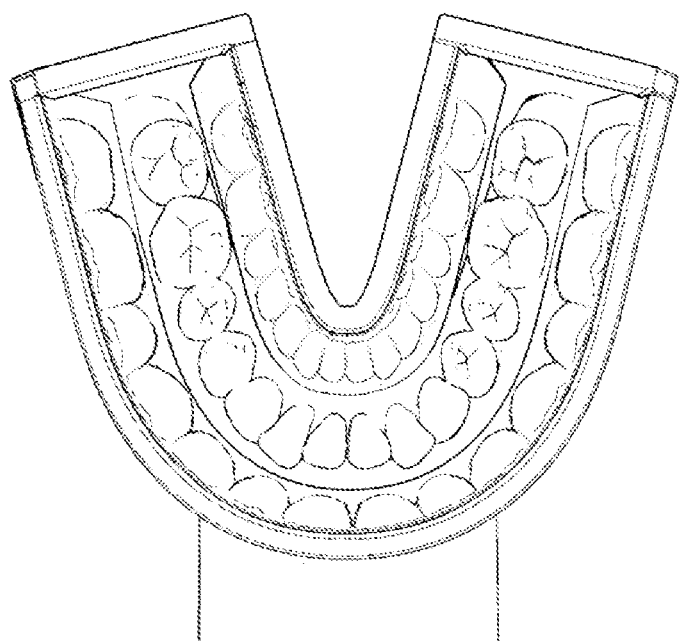
FIG. 12 shows a schematic image captured with invention.

The mouthpiece 30 is configured to be placed inside the mouth, as shown in FIGS. 5A and 5B. It comprises of an inner surface 31 and an outer surface 32, which are curved to form a mouthpiece shape. The inner surface 31 and the outer surface 32 are connected together by two bridges 33, leaving a gap between them and the top and the bottom of the mouthpiece are open. The gap and the width of the mouthpiece is wider than the width of the teeth, and therefore, it clears a space around the teeth, exposing both the front and the back surfaces of all teeth, as shown in FIG. 12. The inner 31 and outer 32 surfaces of the mouthpiece are mirror surfaces, and are angled (tilted) such that they reflect images of the back and front surfaces of the teeth outwardly towards the camera. The tilt angle of each curved part of the mouthpiece is configured to be able to image whole surfaces of teeth, from top to bottom, on the mirror surfaces, which is reflected outwardly to a viewer or a camera. Mouthpiece also is designed in different sizes so it can be fitted in different size of mouths, according to age and jaw shape of consumer.

Figure 6:
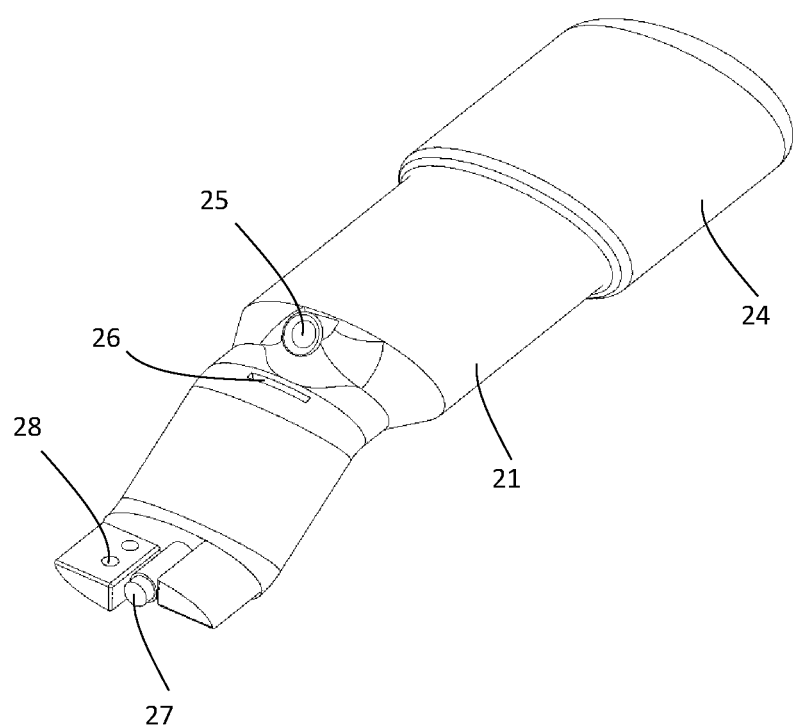
FIG. 6 shows details of the handle of the invention.

Again, as shown in FIGS. 5A, 5B and 6, connection of mouthpiece 30 and the handle 20 is detachable so that the mouthpiece 30 can be removed to wash and be disinfected. In one embodiment, the mouthpiece connection handle 20 is an elliptical shape connection with a hole 34 at the center which aligns with the male part 27 of the handle 20 to works as a male and female connection and then one pair of edges around this hole 34 to match with handle 20 connection part and finally one pair of holes 35 on each edge for small cylindrical magnets 50 to place in to hold this connection.

Figure 1A:
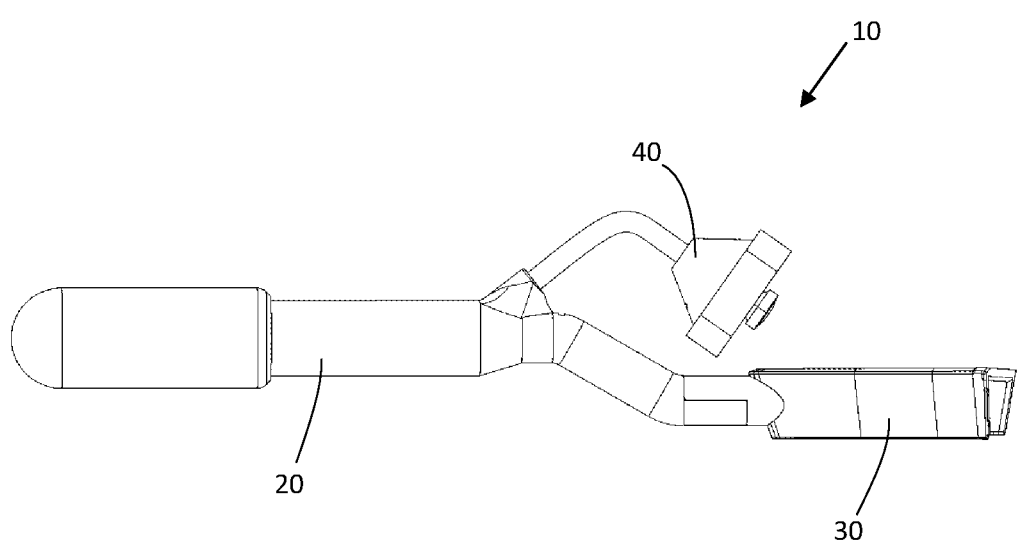
FIG. 1A shows the embodiment of the invention.
Figure 1B:
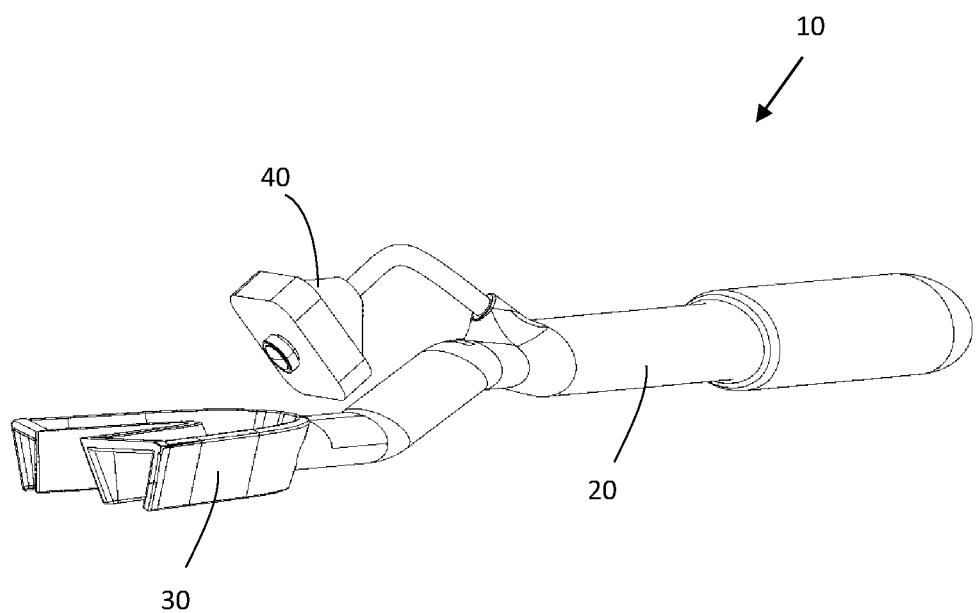
FIG. 1B shows another view of the embodiment of the invention.
Figure 2A:
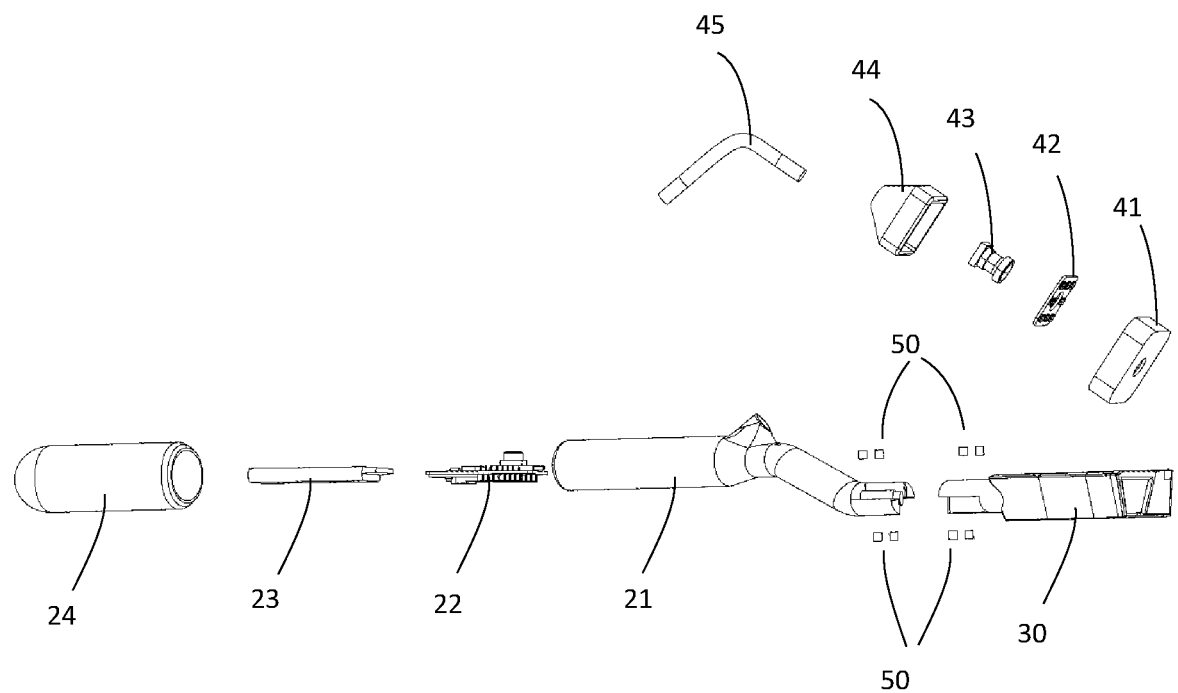
FIG. 2A shows the exploded view of the invention.
Figure 2B:
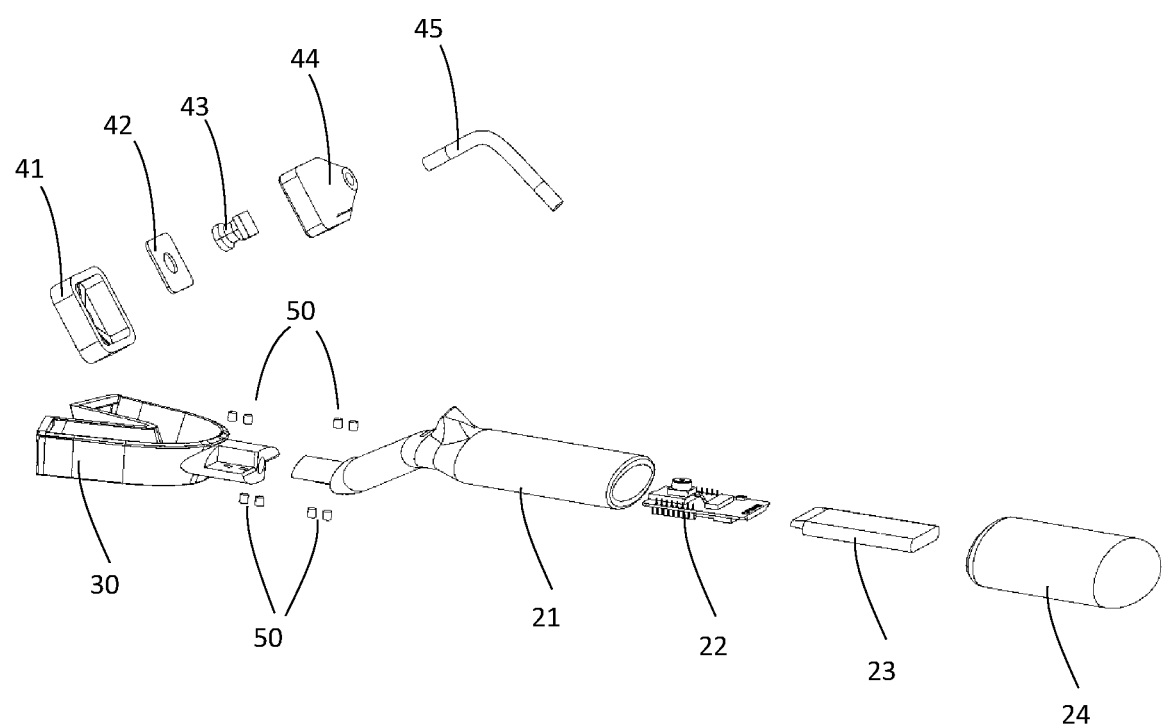
FIG. 2B shows another side of the exploded view of the invention.
Figure 3:
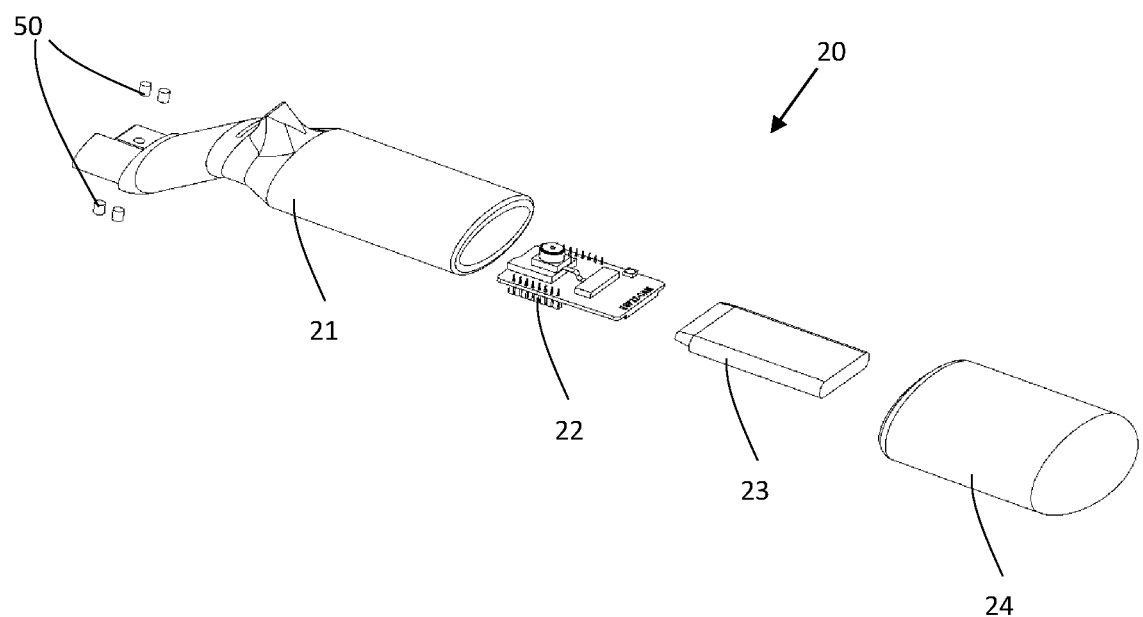
FIG. 3 shows the exploded view of the handle of the invention.
Figure 4:
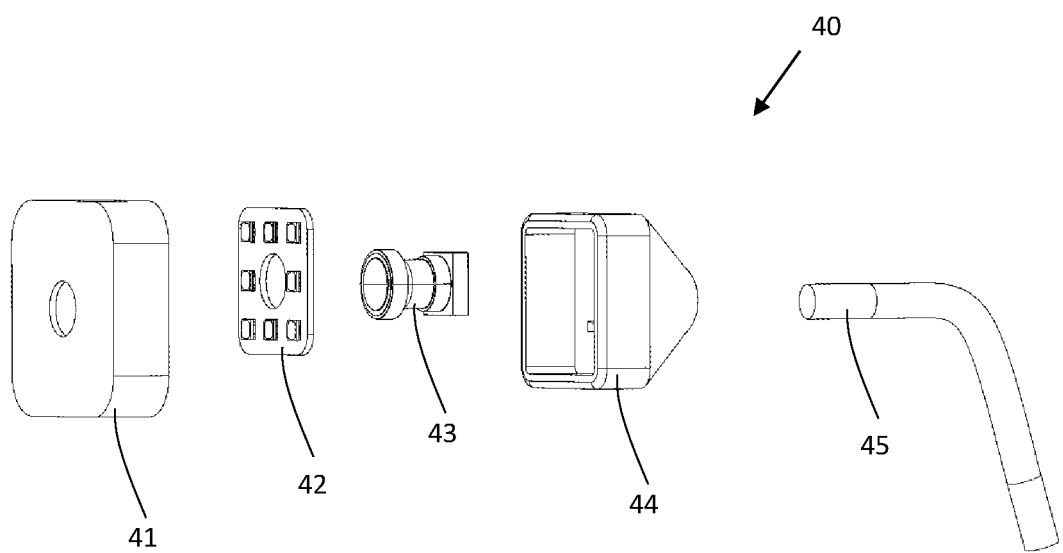
FIG. 4 shows the exploded view of the camera stand of the invention.

The camera stand 40 comprises of a camera 43 and a light source 42, which are placed in a camera housing 44, as shown in FIG. 4. A thin blurry cap 41 is also provided to protect camera 43 and light source 42. The camera-stand 40 connects to the handle 20 with a flexible spring pipe 45 to allow adjustment of the camera position. The camera-stand 40 can move and rotate easily and stays wherever it is left. FIGS. 2A and 2B show exploded views of the device. The camera 43 communicates over a wired or wireless data communication channel with external devices, such as a mobile device, to receive images and process them and provide output image data that can be stored and displayed.

Battery 23 and a control board 22 are placed inside the handle. In a preferred embodiment, the handle 20 comprising of two elliptical shells: a handle cap 24 and a handle base 21 that connect together. A battery 23 and electrical board 22 are placed inside handle cap 24 and handle base 21, respectively. Rechargeable battery 23 supply power for electrical components of device 10. Electrical board 22 connects to smart phone or tablet or computer via Bluetooth or WIFI or cable and controls the operation of the light source 42 and the camera 43, to take pictures and share them with connected smart devices.

Handle base 21 comprises of a connection means 25 to the flexible spring pipe 45, two pair of holes 28 for small cylindrical magnets 50 and a groove 26 that flat cable and wires for camera 43 and light source 42 come out from battery 23 and board 22. Handle cap 24 placed at the end of the handle base 21 and in addition to covering it, also has an empty space inside for battery 23. Electrical board 22 places inside handle base 21 and is the command center where connects to an outside smart phone or a computer and helps user to turn on and off the light source 42 and take pictures by camera 43. Rechargeable battery 23 supplies power to electrical board 22, camera 43 and light source 42.

FIG. 4 shows the exploded view of camera stand 40 with more details. Camera housing 44 is connected to the flexible spring pipe 45 at the end and one thin blurry cap 41 at front where camera 43 and light source 42 are placed in camera housing 44. Flexible spring pipe 45 provides ability for camera housing 44 to be moved and rotated by a user and stay still wherever it is left.

Figure 7:
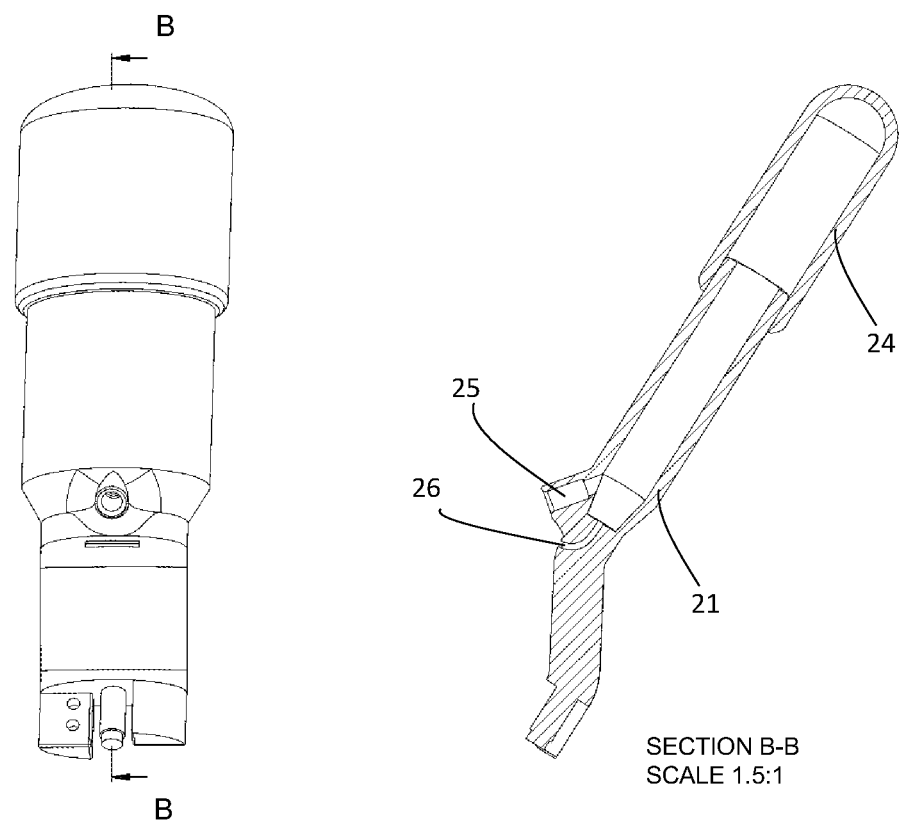
FIG. 7 shows a section view of the handle of the invention.

FIGS. 5A, 5B and 6 show the connecting means of the handle to the mouthpiece. The handle 20, which has a male 27 and female 34 connection and four pairs of small cylindrical magnets 50 connects to the mouthpiece, which has the female 34 counterpart. Mouthpiece 30 and the handle 20 are connected together with a male 27 and female 34 connection and hold by four pair of small cylindrical magnets 50 in their position. FIG. 6 shows more details of the handle 20. In front side of the handle 20 has a male part 27 to connect to mouthpiece 40 and two wedges that couple with the mouthpiece 40. Each wedge has a pair of holes 28 for magnets 50 to be placed in. A groove 26 is provided for camera 43 cable and light source 42 wires to go into the handle 20 to connect to electrical board 22 and battery 23. Behind the groove 26 there is the connection place 25 which is the place where the flexible spring pipe 45 connects to the handle 20. FIG. 7 shows a cross-sectional view of the handle 20 with more details of the inside of the handle 20 and channels in it. It shows the empty space inside the handle base 21 and handle cap 24 where electrical board 22 and battery 23 are placed in.

Figure 8A:
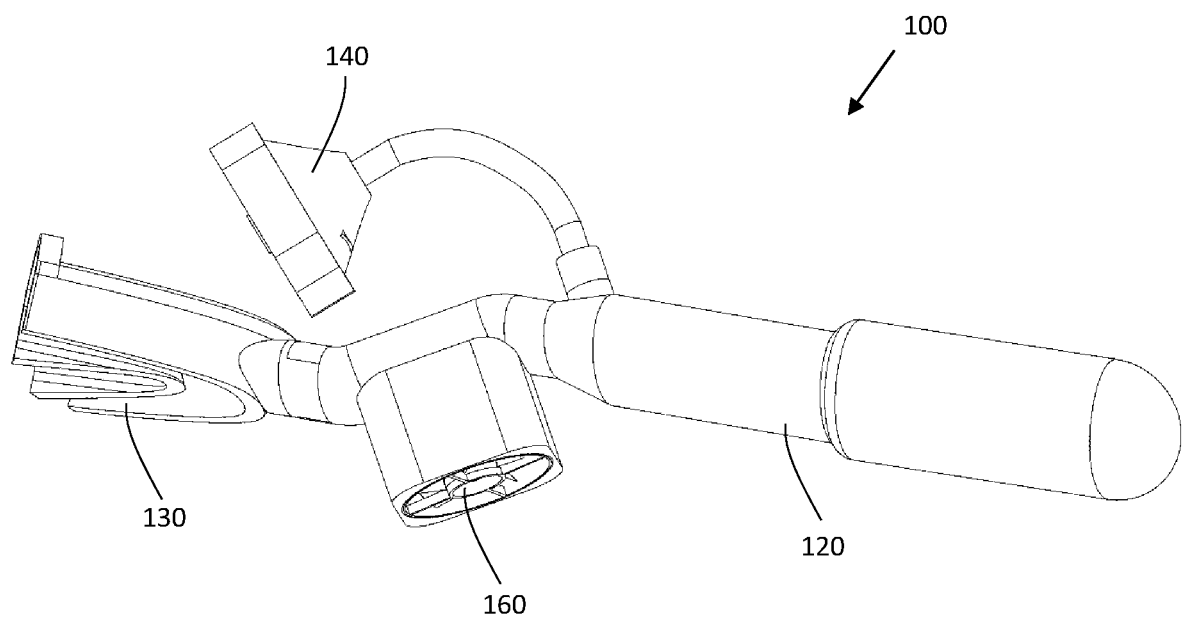
FIG. 8A shows another embodiment of the invention with fan.
Figure 8B:
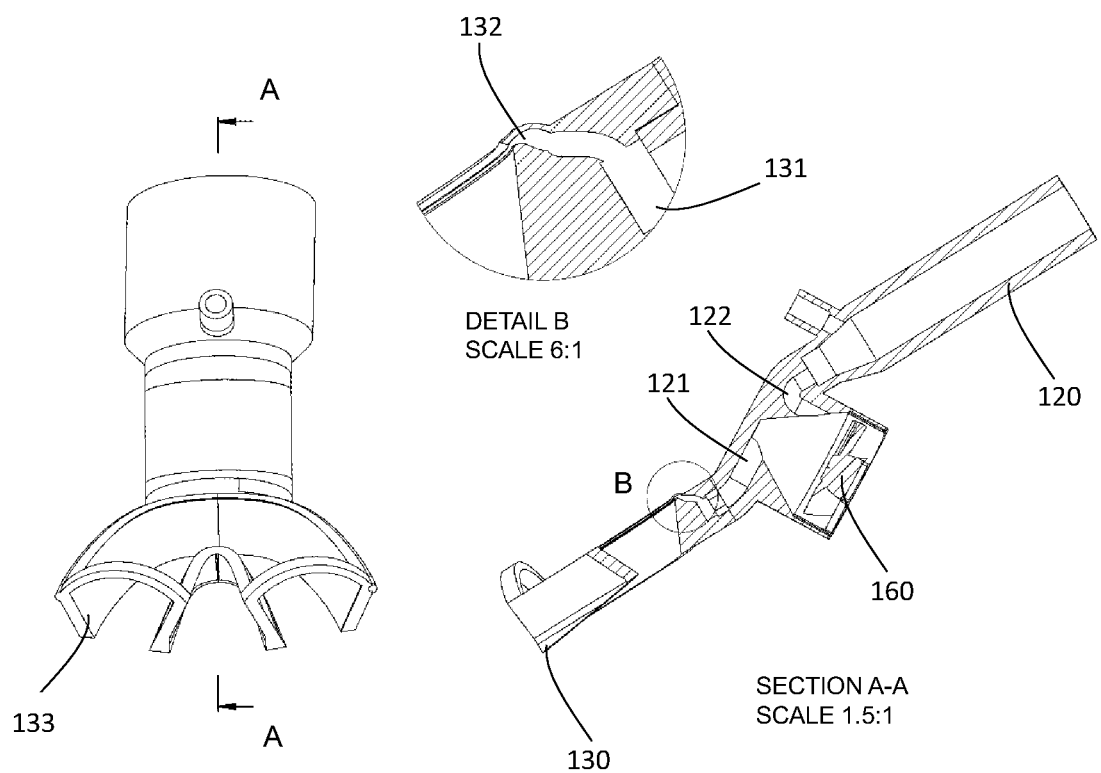
FIG. 8B shows a section view of another embodiment of the invention with fan.

FIGS. 8A and 8B show another embodiment 100 of the present invention with a fan 160. Exhaled air is warm and moist, therefore the mirrors in the mouthpiece 130 can become foggy. To keep the mirrors clear, a fan 160 is provided to force airflow on the surfaces of the mirrors. In this embodiment a fan 160 is placed in front of the handle 120 near the connection to the mouthpiece 130. The fan 160 forces air to flow through an air channel 121 in the handle 120, which ends to another air channel 131 in mouthpiece 130, which is connected to another air channel 132 on the top of external curve 133 of the mouthpiece 130. Therefore, air is forced through the space inside mouthpiece 130 and teeth to avoid mirrors to become foggy. The fan 160 is connected to the electrical board 122 and battery 123 through a channel 122, which is between fan 160 and inside of the handle 120.

Figure 9A:
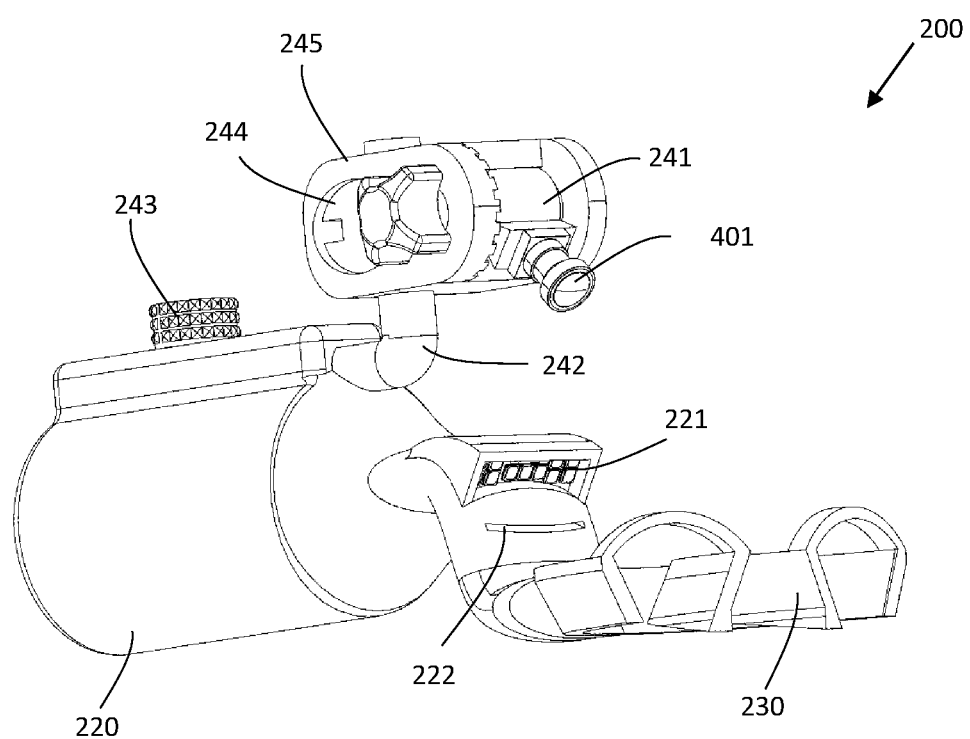
FIG. 9A shows another embodiment of the invention with camera on adjustable movement mechanism.
Figure 9B:
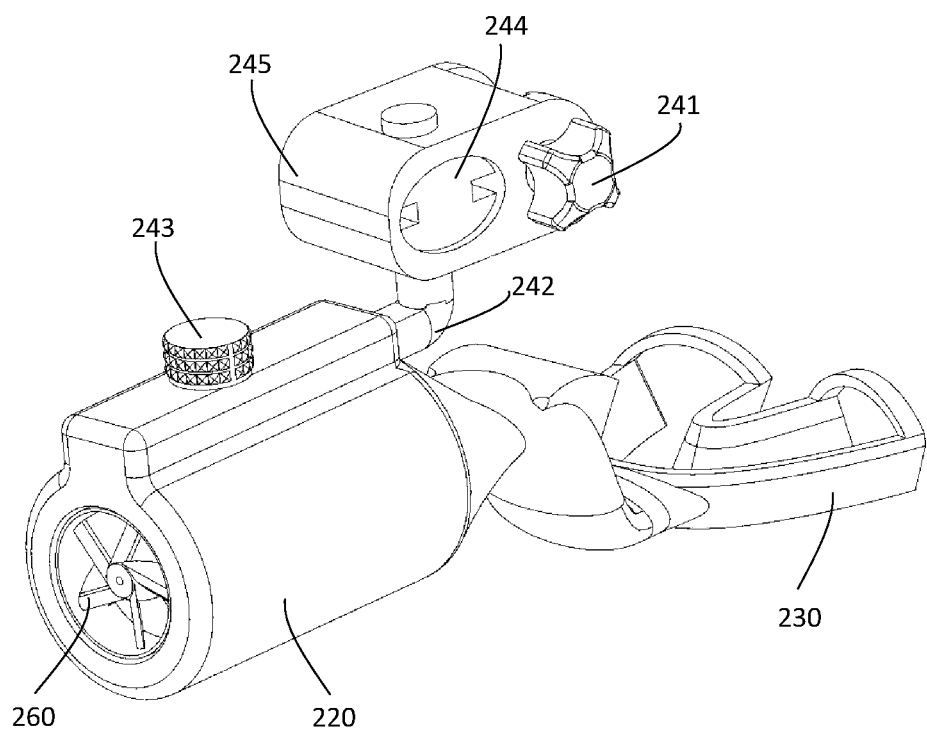
FIG. 9B shows another view of another embodiment of the invention with camera on adjustable movement mechanism.

FIGS. 9A and 9B show another embodiment of the invention with a camera 401 on the adjustable movement mechanism 240. Camera 401 is placed on a rotatable shaft 241, which can rotate around its axis by the user to change the angle of the camera 401 towards the mouthpiece 230. Rotatable shaft 241 is a part of the body 245, which can move up and down on an L-shaped shaft 242. By a little push on button 244 then the body 240 is free to move up and down on the L-shaped shaft 242 and become locked when the button 244 is no longer pushed. L-shaped shaft 242 goes in a hole and becomes tighten with a screw 243. By loosening the screw 243, the whole mechanism, including L-shaped shaft 242, the body 245 attached to that and camera 401 on the body 245 become free to move forward and backward. A fan 260 placed at the end of the handle 220 makes an air flow through it and ending to a groove 222 in front side of the handle 220 facing mouthpiece 230, so uniform air flow comes out of this groove 222 to inside space of mouthpiece 230 to prevent mirrors to become foggy. A light source 221 is placed on the front side of the handle 220 and above the air groove 222 to illuminate the imaging zone uniformly.

Figure 10A:
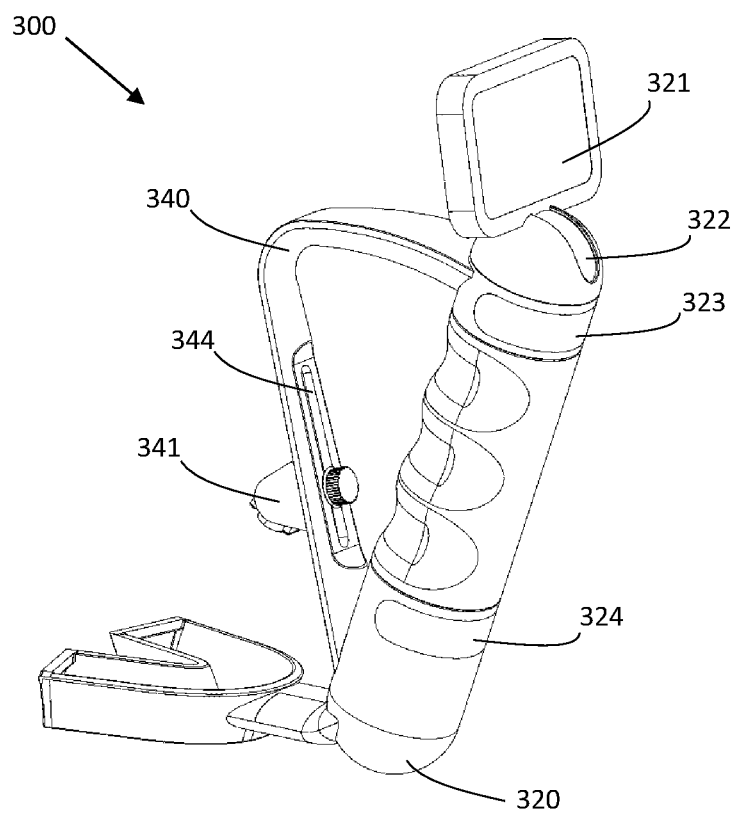
FIG. 10A shows another embodiment of the invention with monitor.
Figure 10B:
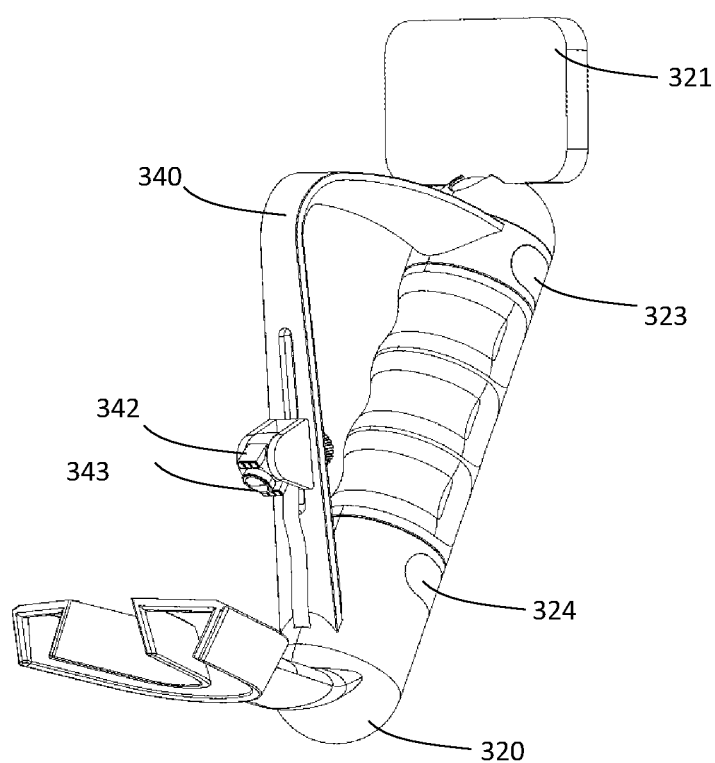
FIG. 10B shows another view of another embodiment of the invention with monitor.

FIGS. 10A and 10B show another embodiment of the invention with a monitor 321. The handle 320 is designed to be perpendicular to the mouthpiece 330. The camera stand is placed on the handle 320. The camera 343 and the light source 342 are placed on a wagon 341, which can go up and down in a rail 344, which is placed on a curve 340 as a part of the handle 320. There are two buttons 323,324 on the handle 320 to turn on monitor 321 and the light source 342, and also to take pictures with the camera 343. The upper button 323 is for taking picture of the lower teeth, therefore, it can be easily touched by figures. The lower button 324 is for taking pictures of the upper teeth, to be touched by figures. Monitor 321 is placed on a round base 322, which can rotate around its center, therefore the monitor 321 can rotate to provide a better angle to look.

Figure 11:
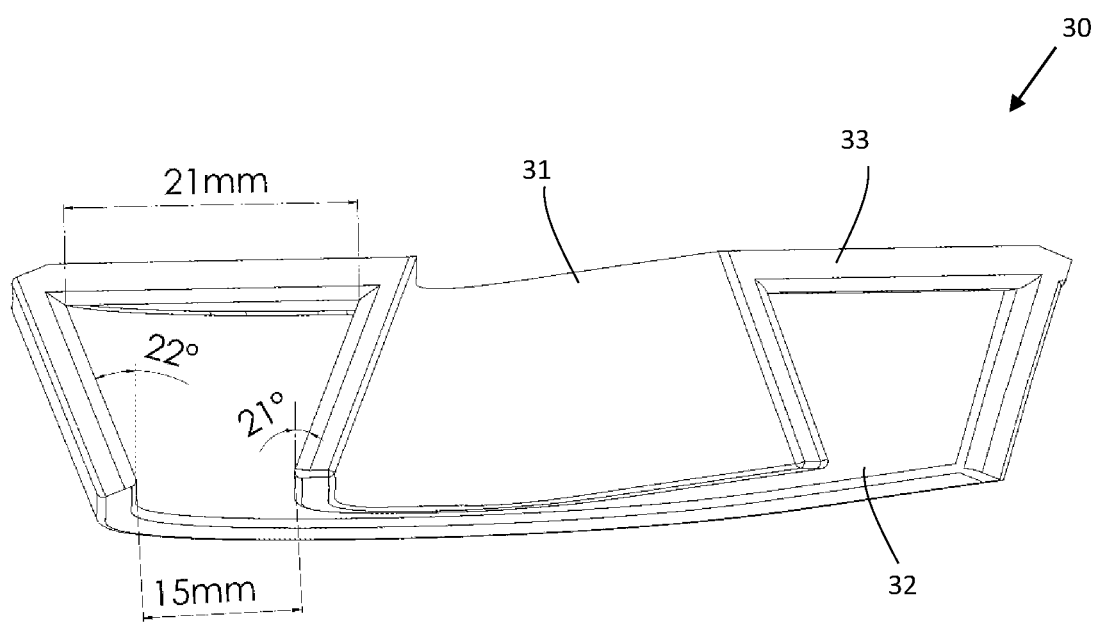
FIG. 11 shows gap distance and tilt angle between first and second surfaces of mouthpiece to the vertical line.

FIG. 11 shows tilt angle of inner surface 31 and outer surface 32 than the vertical axis and also minimum (at the base) and maximum (at the top) gap between two surfaces. Tilt angle decided in a way that an outside viewer can see whole surfaces of teeth including inside, outside and top of teeth in order to inner surface, outer surface and directly. Base on this description, tilt angle for this embodiment can be between 20 to 30 degrees from vertical axis and minimum gap is between 0.5 to 2.5 cm and maximum gap is between 1 to 3 cm.

FIG. 12 shows a schematic image captured with invention. In this image the top of teeth is shot directly and inner surfaces of teeth are reflected from inner surface 31 of mouthpiece and outer surfaces of teeth are reflected from outer surface 32 of mouthpiece, so entire surfaces of teeth are shown in one image which was the main reason to design this mouthpiece.

Figure 13:
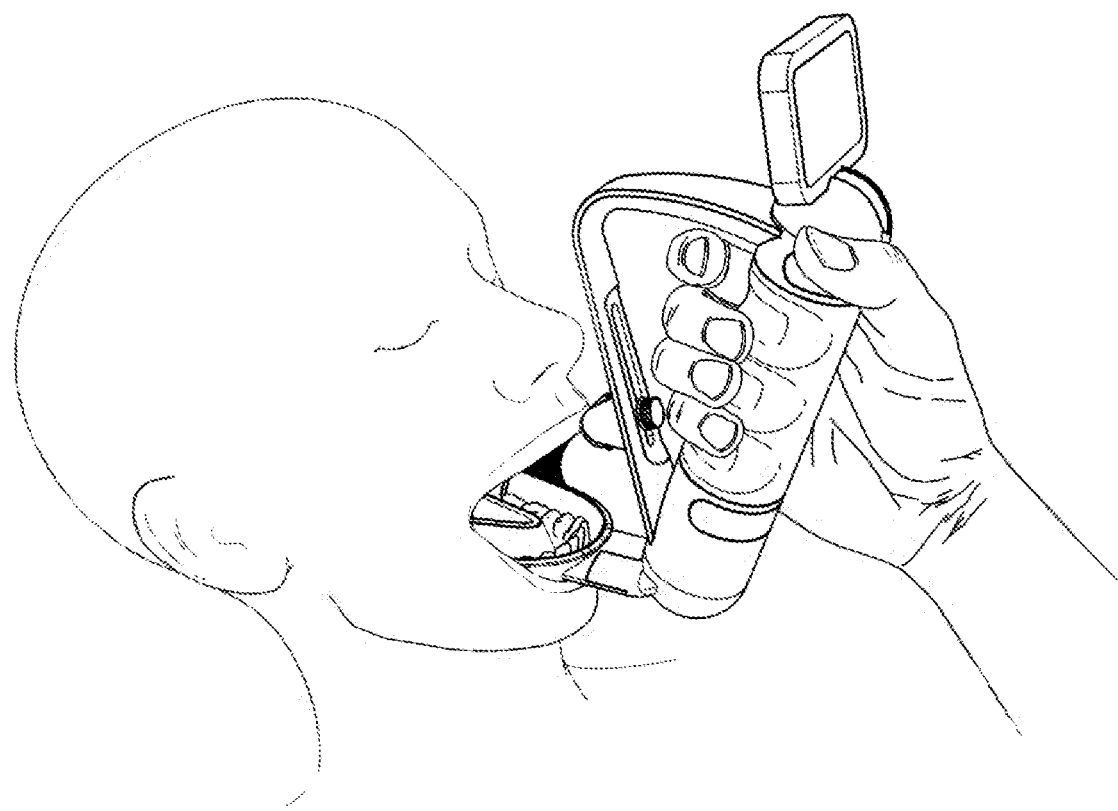
FIG. 13 shows one embodiment of the invention in use.

FIG. 13 shows one embodiment of the invention in use where the position of handle in hand, position of mouthpiece in mouth and position of camera than mouthpiece is shown. Mouthpiece places on upper or lower jaw and teeth stay on the gap between inner and outer surfaces of mouthpiece where online image is displaying on monitor for consumer to move and rotate handle by his hand to find proper position of mouthpiece and camera to take an acceptable image from teeth.

In one embodiment, four different light sources for both normal and florescence imaging are embedded in the system. These are white (400-700 nm), UV LED-diodes (385-400 nm), amber and green (520-530 nm). The device further uses two high pass filters conjugation with above mentioned light resources. The filters can be selected from bandpass filters and high pass filters to prevent unnecessary light wavelengths and enhance the imaging quality. The UV and green light sources excite the teeth and gum with the related filter in order to enhance the differentiation in the captured images. The amber light enhances the tissues reflectance to directly observe the tissue which can be used to make a tentative diagnosis. The light sources are emitted along the surface of tooth. The oral camera is then used to captures the image at different times in order to determine information about the tooth surface. The images can be generated in any of a number of ways. Once the images are captured computation techniques well known to those skilled in the surface imaging arts will analyze the captured images. The images are saved on the phone and the image analysis software compares the images of the teeth over time, and identifies any changes in the teeth.

Fluorescence-based imaging method as an effective solution operates on these principles. (1) A healthy tooth enamel yields a higher intensity of fluorescence under excitation from some wavelengths compared with de-mineralized enamel which has been damaged by caries infection. The strong correlation between mineral loss and loss of fluorescence for blue light excitation is then used to identify and assess carious areas of the tooth. (2) A different relationship has been found for red light excitation, a region of the spectrum for which bacteria and bacterial by-products in various regions absorb and fluoresce more pronouncedly than do healthy areas. (3) Porphyrins emits red fluorescence, which is related to metabolize by bacteria in plaque, calculus, or an infected carious lesion. Near-UV LED can provide the excitation light for red fluorescence imaging of dental plaque. Therefore, the technology based on the principle of fluorescence provide a high image quality to diagnose and treat caries. It offers the ability to detect tooth decay at different stages of its development allowing the dentist to determine the most effective course of treatment.

The oral camera system also has a software application to save and compare the captured images over time, using image processing and machine learning and analyzes the captured images and recognizes the issues with the teeth. The results of the analysis are reported to the user and the dentist. The deep learning methods provide an accurate and rapid analysis of the image. The image analysis will determine the following conditions: the level of plaque, the level of wear, calculus, gingivitis, fluorosis, dental trauma, pulp polyps, tooth wear, tooth contour and other symptoms.

A use of the present device is for patients going through chemical therapy and radiotherapy in order to closely monitor the oral mucosa. For example, in some cases, about two weeks after radiotherapy, some patients develop mucositis (inflamed mucosa) and candidiasis. In these patients, regularly taking oral pictures can be helpful in prescribing preventative medication and controlling complications, improving quality of life.

Another use of the present device is in patients consuming Bis-phosphonate drugs (used for controlling osteoporosis). In these cases, there is chance of the patients developing MRONJ (Medication-Related Osteonecrosis of the Jaw). Gradual changes in soft tissue due to a limitation in angiogenesis can be seen by capturing oral images on a regular basis.

The invention claimed is:
1. An oral camera, comprising:
a) a mouthpiece configured to be placed on an upper or a lower jaw of a user, the mouthpiece comprising:
  i) an inner curved part and an outer curved part configured to respectively be placed on an inner side and an outer side of teeth of the lower or the upper jaw of the user, and wherein the inner curved part and the outer curved part are connected by a pair of bridges, leaving an open gap between the inner curved part and the outer curved part, and
  ii) the inner curved part has a first mirror surface having a first tilt angle to reflect images of back surfaces of teeth, and the outer curved part has a second mirror surface having a second tilt angle to reflect images of front surfaces of teeth to an outside viewer or a camera system;
b) a handle detachably connected to the mouthpiece;
c) an adjustable camera stand connected to the handle;
d) a camera system connected to the flexible camera stand, the camera system comprising a camera, a light source and optics;
e) a processor to control the operation of the camera and the light source and to communicate with external devices, and
f) a power supply,
  whereby the camera system is adjusted to view back and front surfaces of teeth as reflected by the first and second mirrors, respectively, and the top surfaces of teeth as directly viewed by the camera.

2. The oral camera of claim 1, wherein the open gap of the mouthpiece is in the range of 1-3 cm at an upper side and 0.5-2.5 cm at a lower side of the mouthpiece.

3. The oral camera of claim 1, wherein the first and the second tilt angle is in the range of 20 to 30 degrees with respect to a vertical axis.

4. The oral camera of claim 1, wherein the handle is aligned in the same direction as or an oblique direction to the mouthpiece.

5. The oral camera of claim 1, wherein the handle is aligned in a perpendicular direction as the mouthpiece.

6. The oral camera of claim 1, wherein the first mirror and the second mirror comprise of a plurality of flat mirrors that are placed on the inner and outer curved parts of the mouthpiece, thereby providing undeformed images of back and front surfaces of teeth.

7. The oral camera of claim 1, wherein the first mirror and the second mirror comprise of a plurality of convex mirrors that are placed on the inner and outer curved parts of the mouthpiece, thereby providing expanded images of back and front surfaces teeth.

8. The oral camera of claim 1, wherein the adjustable camera stand is a flexible spring pipe having adjustable length to change a distance and an angle between the camera and the mouthpiece.

9. The oral camera of claim 1, further having a monitor rotatably attached to the handle to allow a user to view the images of teeth directly on the monitor.

10. The oral camera of claim 1, further having a fan to provide a constant flow of air through the mouthpiece to keep the mirrors clear.

11. The oral camera of claim 1, wherein the camera system is a smart phone having a phone camera, and wherein the smart phone is attached to the camera stand.

12. The oral camera of claim 1, wherein the light source is a white (400-700 nm), a UV LED-diode (385-400 nm) and/or an amber and green (520-530 nm) light to generate fluorescence, and
wherein the camera system further comprises of high and low bandpass filters to prevent unnecessary light wavelengths and enhance the imaging quality.

13. The oral camera of claim 1, further having an application configured to detect changes in teeth and to identify cavities and decays.

14. The oral camera of claim 1, wherein the mouthpiece has a set of sizes, each size configured to a jaw size and a jaw shape.

15. The oral camera of claim 1, wherein the handle is attached to the mouthpiece by an attaching mechanism, comprising of a quick connect male-female connector with magnets.

16. The oral camera of claim 1, wherein the mouthpiece is made of silicone and disposable.

17. The oral camera of claim 1, wherein the camera stand comprises of an adjustable movement mechanism, wherein a L-shaped shaft goes toward and backward in a rail on the handle and get fixed with a screw, base part stands on other end of L-shaped shaft and moves with the shaft and goes up and down on this shaft and get fixed with a push button, camera places on a rotatable shaft on base part and rotates around its axis to change angle to mouthpiece.

* * * * *